United States Patent [19]
Huber

[11] 4,042,303
[45] Aug. 16, 1977

[54] METHOD AND APPARATUS FOR AUTOMATED SAMPLING WITH AN ATOMIC ABSORPTION SPECTROMETER

[75] Inventor: Bernhard Werner Huber, Überlingen, Germany

[73] Assignee: Bodenseewerk Perkin-Elmer & Co. GmbH, Überlingen, Germany

[21] Appl. No.: 685,007

[22] Filed: May 10, 1976

[51] Int. Cl.² .......................... G01J 3/30; G01N 21/16
[52] U.S. Cl. .................................. 356/85; 73/425.4 P; 356/244; 356/246
[58] Field of Search .......................... 356/85, 244, 246; 73/425.4 P

[56] References Cited
U.S. PATENT DOCUMENTS

| | | | |
|---|---|---|---|
| 3,671,129 | 6/1972 | Wiedeking | 356/85 |
| 3,704,953 | 12/1972 | Carter et al. | 356/244 |

*Primary Examiner*—Vincent P. McGraw
*Attorney, Agent, or Firm*—S. A. Giarratana; F. L. Masselle

[57] ABSTRACT

Method and apparatus for introducing a sample to be analyzed through an introduction aperture into a graphite tube of a graphite tube cell of an atomic absorption spectrometer, wherein a plurality of sample containers containing the samples to be analyzed are placed in a row in a sample holding device, the sample containers being open at both ends. The sample containers are successively transported to an introduction device and a sample container is inserted into the introduction aperture of the graphite tube by means of the introduction device. The sample is transferred from the sample container into the graphite tube and the sample container is removed therefrom and the next subsequent sample container is transported to the introduction device.

20 Claims, 4 Drawing Figures

METHOD AND APPARATUS FOR AUTOMATED SAMPLING WITH AN ATOMIC ABSORPTION SPECTROMETER

BACKGROUND OF THE INVENTION

This invention relates to method and apparatus for introducing a sample to be analyzed through an introduction aperture into a graphite tube of a heated graphite atomizer of a flameless atomic absorption spectrometer.

In flameless atomic absorption, the atomic cloud, whose absorption is measured, is generated in a graphite tube of a heated graphite atomizer. The sample to be analyzed is in general introduced through a wall aperture into the graphite tube. Only very small quantities, of the order of up to about 20 microliters, for example, are normally introduced by means of a micro-pipette into the graphite tube. However, this procedure has certain disadvantages when carrying out a series of atomic absorption measurements, as an unproportionately large amount of time and the continous presence of an operator are required. It is known from gas chromatography, as referred to in German AS 1,157,817, to use so-called micro-dipper bars instead of micro-pipettes, i.e. capillary containers into which liquid volumes of up to 20 microliters are aspirated by means of capillary action.

An object of the present invention resides in the provision of a procedure and a device of the above-mentioned type which, with the use of sample containers open at both ends, carries out an automated measuring series.

SUMMARY OF THE INVENTION

According to the invention the aforesaid problem is solved by the provision of a sample container, open at both ends, which is inserted by means of an introduction device into the introduction aperture of the graphite tube. After a sample has been introduced into the graphite tube, the sample container is returned to the sample holding device and, upon return of the sample container, the next following sample container is transported to the introduction device. In this procedure, the sample containers are filled, independently of the analysis step and placed in the sample holding device. A specific advantage of this procedure consists in the fact that, during the time when the measuring series is being carried out, the sample containers can be inserted one after the other into the introduction aperture of the graphite tube, whereby the sample is introduced in a particularly simple manner.

According to one aspect of the invention, the sample container, positioned above the introduction aperture of the graphite tube, is forced into the introduction aperture by means of the introduction device, against the tension of a spring, and kept in this position until the sample has been transferred into the graphite tube. The application of the spring tension makes sure that the sample container always follows the individual movements of the introduction device.

According to another aspect of the invention, the sample is transferred into the graphite tube by means of a gas flow directed through the introduction device, when it is in its pressed-down position. Part of the inert gas stream, passing through the heated graphite atomizer, can be used for this purpose by directing it through the sample container when the introduction device is in the down-position.

It will be appreciated that the sample containers offer the advantage of retaining the sample liquid in them by capillary action, but then additional measures have to be taken for transferring the sample from the sample container into the graphite tube. Part of the inert gas, indispensable for the operation of the heated graphite atomizer, is advantageously used for this purpose.

In one form of the invention there is provided a new and improved device for introducing a sample to be analyzed through an introduction aperture into a graphite tube of a graphite tube cell of an atomic absorption spectrometer comprising a sample holding device for stepwise movement into a sampling position above the heated graphite atomizer. Sample containers are provided in the form of micro-pipette tips, open at both ends, which when in their sampling positions, are positioned in alignment with the introduction aperture of the graphite tube. The introduction device comprises a sliding member movable vertically in a guide, which places the sample container into the introduction aperture. In the down-position of the sliding member the sample container is connected to a pressure source to press the sample into the graphite tube. A control device is provided which controls the operation of the introduction device and the sample holding device, thereby controlling the analysis of one sample after the other.

According to one aspect of the intention, a common support is provided for the sample holding device and the introduction device, and the heated graphite atomizer is removably attached to this support. Thus, the individual elements are located and maintained in their usual positions with respect to each other.

In one form of the invention the sample holding device is in the form of a turntale having mounting means for the micro-pipette tips disposed adjacent the circumference thereof. This mounting means includes a spring-loaded holding member adapted for vertical reciprocating movement with respect to the turntable. The holding member has an arm portion extending outwardly of the periphery of the turntable, and an aperture is provided therein for receiving the micro-pipette tips.

Further, according to the invention, the sliding member is mounted above the turntable and is provided with a lower punch-like element that engages the sample container to urge the micro-pipette into the introduction aperture of the graphite tube when in its down-position. Spring means are provided to urge the sliding member towards its upper position. The sliding member is provided with a longitudinally extending gas duct having an exit opening at the bottom thereof. The upper end of the gas duct is connectible to an inert gas supply through a control valve so that, when the sliding member is in its down-position, gas passes downwardly through the gas duct to force the sample out of the micro-pipette tip into the graphite tube. This gas flow also serves to seal the top of the micro-pipette. In one form of the invention, the inert gas is supplied from the inert gas stream passing through the heated graphite atomizer.

According to the invention, means are provided for effecting the vertical movement of the sliding member. In one form thereof, this means comprises an electric motor, which is controlled by a device, provided for the purpose. In another form of the invention, the means for effecting vertical movement comprises a pneumatic drive system. In this system the sliding member is in the form of a piston and rod assembly and the guide is in the form of a pneumatic cylinder. Control means are provided for admitting inert gas at the top of the cylinder to urge the sliding member downwardly. According to one aspect of the invention this inert gas is from the inert gas stream passing through the heated graphite atomizer.

BRIEF DESCRIPTION OF THE DRAWINGS

FIG. 3 is a fragmentary view, partially in diagramatic form, showing alternative means for moving the sliding member.

DETAILED DESCRIPTION OF PREFERRED EMBODIMENTS

Figures 1, 2:
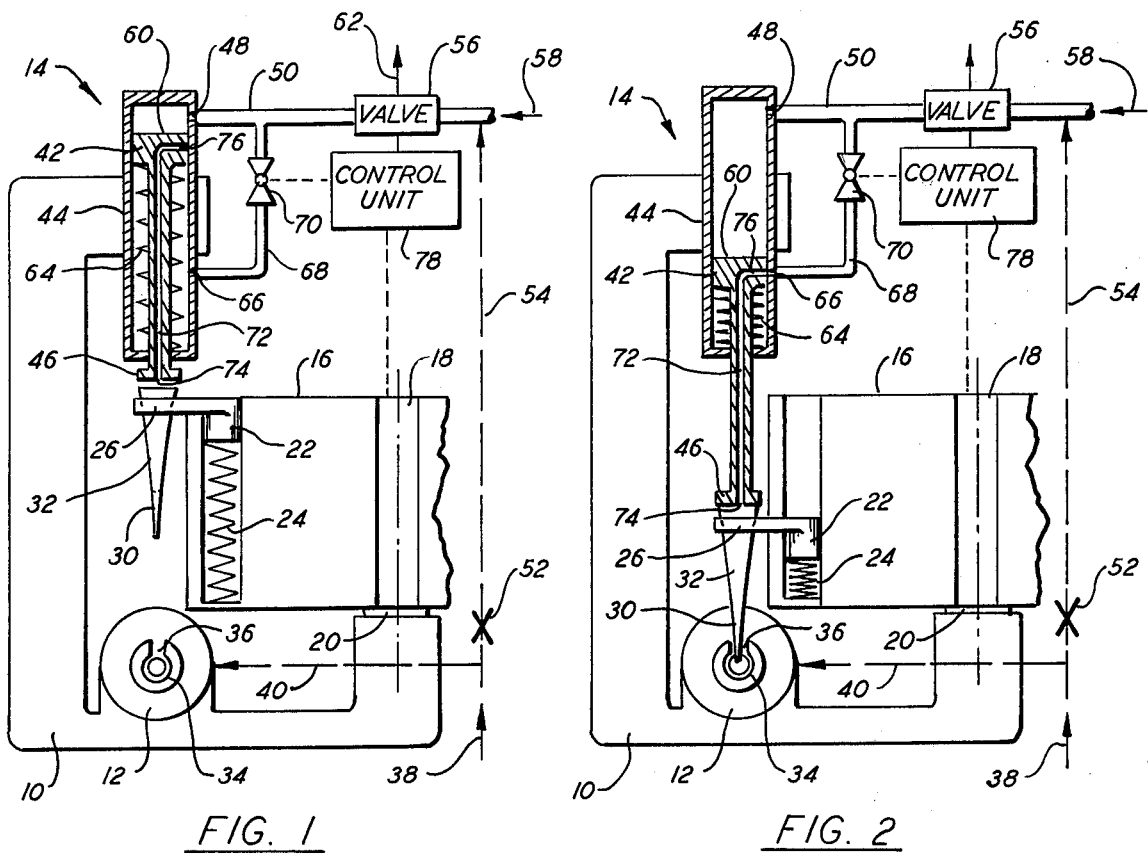
FIG. 1 is a side elevation, partially in section, of a device for introducing a sample to be analyzed through an introduction aperture into a graphite tube of a graphite tube cell of an atomic absorption spectrometer according to the invention, when the device is in its rest position.
FIG. 2 is a view similar to FIG. 1, but showing the device in its operative position.
Figures 3, 4:
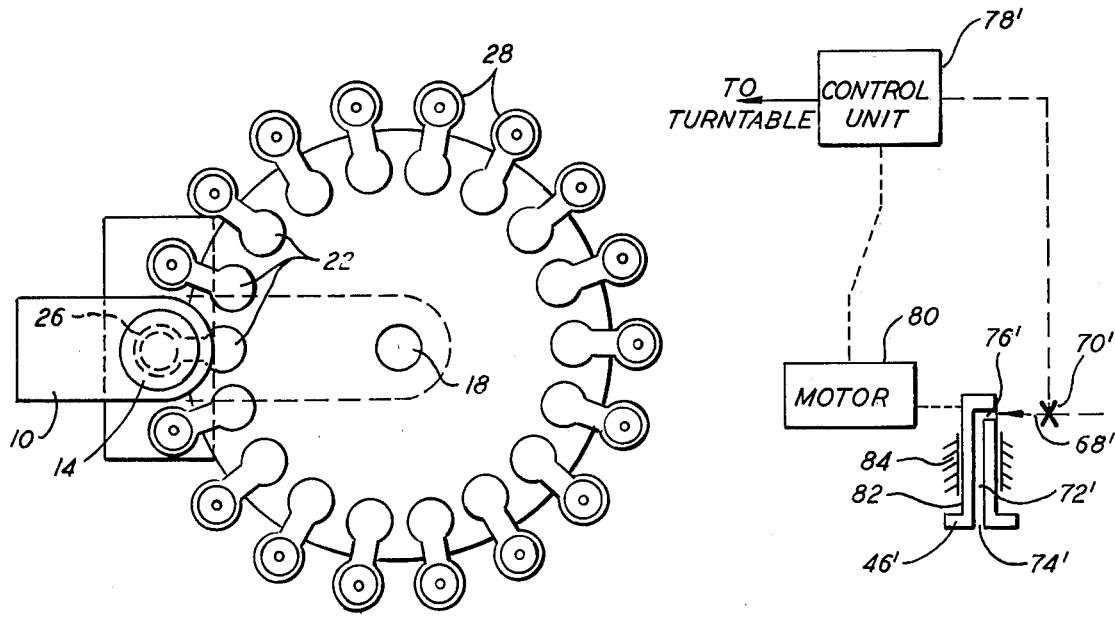
FIG. 3. is a plan view of the device of FIG. 1.

As illustrated in FIGS. 1 to 3, the device, according to the invention, includes a support member 10, a heated graphite atomizer 12 detachably mounted thereon, and an introduction device indicated generally at 14 mounted on the support member 10 above the atomizer 12. A sample holding device in the form of a turntable 16 is mounted on a shaft 18 for stepwise rotation by conventional means, not shown. The shaft 18 is carried by the support member 10, as at 20, whereby, the support member 10 determines the relative positional relationships of the turntable, the heated graphite atomizer and the introduction device, with respect to each other. The turntable 16 carries a sample holding member 22, which is arranged for vertical movement with respect thereto. A spring 24 serves to urge the holding member towards its upper position. The holding member has an arm portion 26 extending outwardly of the periphery of the turntable and an aperture 28 is provided therein for receiving a sample container. The sample containers are in the form of micro-pipette tips 30, that are open at both ends, the sample 32 being contained therein by means of capillary action. Accordingly, a large number of sample containers 30 can be inserted in the holding members 22 of the turntable and kept therein without the sample liquid being lost.

The heated graphite atomizer 12 contains a graphite tube 34 of a graphite tube cell having an introduction aperture 36, which is so-positioned that, when a sample holder holding a micro-pipette tip 30 is in its sampling position, it is in alignment with the introduction aperture 36. A stream of inert gas is passed through the heated graphite atomizer from a source 38 via a pipe line 40, in the conventional manner.

The introduction device 14 includes a sliding member which, in the form of the invention illustrated in FIGS. 1-3, includes a piston and rod assembly 42 mounted in a pneumatic cylinder 44 for vertical reciprocating action. A punch-like element 46 is provided on the lower end of the piston rod for engaging the sample container of the micro-pipette tip 30 to urge it downwardly into the introduction aperture 36. The cylinder 44 has an upper connection 48 connected to a gas line 50. Inert gas may be supplied from the inert gas source 38, through valve 52, line 54 and valve 56. Alternatively, or in addition, inert gas may be supplied from an external source 58. The downstroke of the piston and rod assembly is effected by applying gas under pressure to the top of the piston, as at 60, and the return stroke is effected by relieving the gas pressure on the top of the piston, back through the connection 48, line 50, valve 56 and outlets 62, while spring means 64 acts upwardly on the bottom of the piston.

In addition, the cylinder 44 is provided with a second connection 66, which is connected to the inert gas line 50 via line 68 containing a valve 70. The piston and rod assembly 42 contains a longitudinally extending gas duct 72 having an exit opening 74 at the bottom thereof and an inlet opening 76 at the upper end. As best seen in FIG. 2, the upper inlet opening 76 is in alignmemt with the connection 66 when the piston and rod assembly is in its lower position and, at this time, valve 70 is opened to allow a flow of inert gas under pressure to pass down through the gas duct 72 and into the open upper end of the micro-pipette tip 30 to force the sample 32 out of the micro-pipette tip into the graphite tube 34 of the atomizer 12. It will be appreciated that this gas flow also serves as a seal between the top of the micro-pipette tip 30 and the bottom of the punch-like element 46. A control unit 78 serves to interrelate and control the functions of the valve 56, valve 70 and turntable 16, as will be described more fully hereinafter.

FIG. 4 shows an alternative introduction device. In this embodiment, a motor 80 vertically reciprocates a sliding member 82 in guide 84. The sliding member 82 is provided with a punch-like element 46' and a longitudinally extending gas duct 72' which function in the same manner as their corresponding parts described hereinbefore in connection with the embodiment of FIGS. 1 to 3. A control unit 78' serves to interrelate and control the functions of the motor 80, valve 70' and the turntable 16.

In operation, a plurality of sample containers 30 containing samples are placed in the sample holding members 22, and the control unit 78 actuates the motive means for turntable 16 so that it rotates one step or until one of the sample containers is under the introduction device and over the introduction aperture 36. Then, the control unit 78 actuates valve 56 to close the outlet 62 and open the flow therethrough so that the inert gas under pressure from the supply source flows through line 50 and into the top of the cylinder 44 to thereby urge the piston and rod assembly downwardly from its position as seen in FIG. 1 to its position as seen in FIG. 2. This movement causes the punch-like element 46 to push the micro-pipette tip 30, carried in the holding member 22, downwardly against the force of the spring 24 into the introduction aperture 36 of the graphite tube 34. At the bottom of the stroke, as seen in FIG. 2, the inlet opening 76 is aligned with the connection 66 and the control unit actuates the valve 70 so that inert gas under pressure flows down through the gas duct 72 and into the open top of the micro-pipette tip 30 to thereby force the sample 32 out of the micro-pipette tip and into the graphite tube cell 34 of the atomizer 12. After discharging the sample, the control unit 78 closes the valve 70 and closes the valve 56 with respect to the supply source and opens valve 56 with respect to the outlet 62. This action relieves the pressure on the top of the piston 42 so that the spring means 64 moves the piston and rod assembly back to its upper position. At the same time, the spring 24 returns the holding member 22 to its upper position, as seen in FIG. 1. Thereafter, the control unit 78 actuates the motive means for the turntable 16 so that it rotates one step to position the next adjacent sample container under the introduction device and over the introduction aperture. The aforesaid procedure is then repeated for the next sample analysis.

Thus, an improved introduction device has been shown. Although specific embodiments have been illustrated and described, it will be obvious to those skilled in the art that various modifications may be made without departing from the spirit of the invention, which is intended to be limited solely by the appended claims.

What is claimed is:

1. A method of introducing a sample to be analyzed through an introduction aperture into a graphite tube of a graphite tube cell of an atomic absorption spectrometer, comprising the steps of arranging a plurality of sample containers containing the samples to be analyzed in a row in a sample holding device, said sample containers being open at both ends, successively transporting said sample containers to an introduction device, inserting said sample container into the introduction aperture of the graphite tube by means of said introduction device, transferring the sample into the graphite tube from said sample container, removing the sample container from the introduction aperture and returning it to the sample holding device after the introduction of the sample into the graphite tube, and then transporting the next subsequent sample container to the introduction device.

2. A method of introducing a sample to be analyzed through an introduction aperture into a graphite tube of a graphite tube cell of an atomic absorption spectrometer according to claim 1, wherein said step of transferring the sample into the graphite tube from said sample container comprises arranging the sample container above the introduction aperture of the graphite tube and pressing said sample container, against the force of a spring, into the introduction aperture by means of the introduction device, and holding the sample container in the introduction aperture until transfer of the sample is completed.

3. A method of introducing a sample to be analyzed through an introduction aperture into a graphite tube of a graphite tube cell of an atomic absorption spectrometer according to claim 2 wherein the step of transferring the sample into the graphite tube from the sample container comprises passing a gas flow through the introduction device when the sample container is in the introduction aperture of the graphite tube.

4. A method of introducing a sample to be analyzed through an introduction aperture into a graphite tube of a graphite tube cell of an atomic absorption spectrometer according to claim 3, wherein inert gas is passed through the graphite tube cell, and wherein the gas passed through the introduction device when the sample container is in the introduction aperture is a portion of said inert gas flow.

5. A method of introducing a sample to be analyzed through an introduction aperture into a graphite tube of a graphite tube cell of an atomic absorption spectrometer according to claim 2, wherein inert gas is passed through the graphite tube cell, and wherein the step of pressing said sample container against the force of the spring into the introduction aperture by means of the introduction device is effected by a portion of said inert gas flow engaging a piston-like member in said introduction device.

6. A device for introducing a sample to be analyzed through an inroduction aperture into a graphite tube of a graphite tube cell of an atomic absorption spectrometer comprising, in combination, means for arranging a plurality of sample containers containing the samples to be analyzed in a row on a sample holding device, said sample containers being open at both ends, means for successively transporting said sample containers to an introduction device, means for inserting said sample container into the introduction aperture of the graphite tube by means of said introduction device, means for transferring the sample into the graphite tube from said sample container, means for removing the sample container from the introduction aperture after the introduction of the sample into the graphite tube, and means for transporting the next subsequent container to the introduction device.

7. A device for introducing a sample to be analyzed through an introduction aperture into a graphite tube of a graphite tube cell of an atomic absorption spectrometer comprising, in combination, a sample holding device, a plurality of sample containers containing samples to be analyzed positionable in said sample holding device, said sample containers being configured as micro-pipette tips and being open at both ends, said sample holding device being movable stepwise to move one of said sample containers at a time into a sampling position above the graphite tube cell, an introduction device having a sliding member movable to insert the sample container when in its sampling position into the introduction aperture, means for connecting said sample container to a fluid pressure source for pressing out the sample into the graphite tube when said sample container is in said introduction aperture, and control means controlling the actuation of the introduction device and the movement of the sample holding device.

8. A device according to claim 7 further comprising common support means for said sample holding device and said introduction device, and said graphite tube cell being removably attached to said common support means.

9. A device according to claim 7 wherein said sample holding device comprises a turntable, and said sample holding members are disposed toward the periphery of said turntable for receiving said micro-pipette tips.

10. A device according to claim 9 wherein said holding members are mounted for vertical movement with respect to the turntable, and further comprising spring means for urging the holding members toward their upper positions, respectively.

11. A device according to claim 9 wherein said sliding member is arranged in guide for reciprocating vertical movement above said turntable.

12. A device according to claim 11 further comprising a spring disposed adjacent said sliding member, and said sliding member being arranged to hold said micro-pipette tip in said introduction aperture of the graphite tube against the force of said spring.

13. A device according to claim 12 further comprising means for effecting a gas seal between said sliding member and the adjacent open end of said micro-pipette tip when said micro-pipette tip is in said introduction aperture.

14. A device according to claim 13 wherein said means for connecting said sample container to a fluid pressure source comprises a longitudinally extending gas duct in said sliding member having an exit opening at the bottom thereof adjacent the open end of said micro-pipette tip and having an upper inlet connected to said fluid pressure source, and valve means interposed between said inlet and said fluid pressure source actuatable by said control means when said micro-pipette tip is in said introduction aperture to press out the sample into the graphite tube.

15. A device according to claim 14 further comprising means for passing an inert gas flow through said graphite tube cell, amd wherein said fluid pressure source is connected to said means for passing the inert gas flow through the graphite tube cell.

16. A device according to claim 11 wherein said sliding member comprises a piston and rod assembly and said guide is a cylinder, said cylinder being connected to said fluid pressure source, and valve means being interposed between said cylinder and said fluid pressure source actuatable by said control means to move said piston and rod assembly.

17. A device according to claim 16 further comprising spring means for urging said piston and rod assembly upwardly.

18. A device according to claim 16 further comprisng means for passing an inert gas flow through said graphite tube cell, and wherein said fluid source is connected to said means for passing the inert gas flow through the graphite tube cell.

19. A device according to claim 11 wherein said sliding member is reciprocated by an electric motor controlled by said control means.

20. A device according to claim 7 wherein said sample holding device includes a turntable, and said sample holding members are disposed toward the periphery of said turntable for receiving said micro-pipette tips, and wherein said holding members are mounted for vertical movement with respect to the turntable, and further including spring means for urging the holding members toward their upper positions, respectively, and wherein said means for connecting said sample container to a fluid pressure source includes a longitudinally extending gas duct in said sliding member having an exit opening at the bottom thereof adjacent the open end of said micro-pipette tip and having an upper inlet connected to said fluid pressure source, and valve means interposed between said inlet and said fluid pressure source actuatable by said control means when said micro-pipette tip is in said introduction aperture to press out the sample into the graphite tube, and further including means for passing an inert gas flow through said graphite tube cell, and wherein said fluid pressure source is connected to said means for passing the inert gas flow through the graphite tube cell, and wherein said sliding member includes a piston and rod assembly mounted in a cylinder, said cylinder being connected to said fluid pressure source and valve means interposed between said cylinder and said fluid pressure source actuatably by said control means to move said piston and rod assembly downwardly, spring means for urging said piston and rod assembly upwardly, said second fluid pressure source being connected to said means for passing inert gas flow through the graphite tube cell.

* * * * *

UNITED STATES PATENT AND TRADEMARK OFFICE
CERTIFICATE OF CORRECTION

PATENT NO. : 4,042,303
DATED : August 16, 1977
INVENTOR(S) : Bernhard Werner Huber It is certified that error appears in the above-identified patent and that said Letters Patent are hereby corrected as shown below:

Column 2, line 30, change "intention" to --invention--;

line 35, change "usual" to --mutual--;

line 37, change "turntale" to --turntable--.

Column 3, line 20, change "FIG. 3" to --FIG. 4--.

Column 7, line 9, change "amd" to --and--.

Signed and Sealed this

Thirteenth Day of December 1977

[SEAL]

Attest:

RUTH C. MASON
Attesting Officer

LUTRELLE F. PARKER
Acting Commissioner of Patents and Trademarks